US009901539B2

(12) United States Patent
Finn et al.

(10) Patent No.: US 9,901,539 B2
(45) Date of Patent: *Feb. 27, 2018

(54) TRANSMUCOSAL DRUG DELIVERY DEVICES FOR USE IN CHRONIC PAIN RELIEF

(71) Applicant: BioDelivery Sciences International, Inc., Raleigh, NC (US)

(72) Inventors: Andrew Finn, Raleigh, NC (US); Niraj Vasisht, Cary, NC (US)

(73) Assignee: BioDelivery Sciences International, Inc., Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/724,959

(22) Filed: Dec. 21, 2012

(65) Prior Publication Data

US 2014/0178440 A1 Jun. 26, 2014
US 2017/0035688 A9 Feb. 9, 2017

Related U.S. Application Data (60) Provisional application No. 61/578,755, filed on Dec. 21, 2011.

(51) Int. Cl.
*A61K 9/00* (2006.01)
*A61K 31/485* (2006.01)

(52) U.S. Cl.
CPC .............. *A61K 9/00* (2013.01); *A61K 9/006* (2013.01); *A61K 31/485* (2013.01)

(58) Field of Classification Search
None
See application file for complete search history.

(56) References Cited

U.S. PATENT DOCUMENTS

| | | |
|---|---|---|
| 3,640,741 A | 2/1972 | Etes |
| 3,996,934 A | 12/1976 | Zaffaroni |
| 4,226,848 A | 10/1980 | Nagai et al. |
| 4,250,163 A | 2/1981 | Nagai et al. |
| 4,285,934 A | 8/1981 | Tinnell |
| 4,286,592 A | 9/1981 | Chandrasekaran |
| 4,292,299 A | 9/1981 | Suzuki et al. |
| 4,381,296 A | 4/1983 | Tinnell |
| 4,517,173 A | 5/1985 | Kizawa et al. |
| 4,518,721 A | 5/1985 | Dhabhar et al. |
| 4,552,751 A | 11/1985 | Inaba et al. |
| 4,572,832 A | 2/1986 | Kigasawa et al. |
| 4,582,835 A | 4/1986 | Lewis et al. |
| 4,594,240 A | 6/1986 | Kawata et al. |
| 4,668,232 A | 5/1987 | Cordes et al. |
| 4,713,239 A | 12/1987 | Babaian et al. |
| 4,713,243 A | 12/1987 | Schiraldi et al. |
| 4,713,246 A | 12/1987 | Begum et al. |
| 4,715,369 A | 12/1987 | Suzuki et al. |
| 4,720,387 A | 1/1988 | Sakamoto et al. |
| 4,740,365 A | 4/1988 | Yukimatsu et al. |
| 4,755,386 A | 7/1988 | Hsiao et al. |
| 4,764,378 A | 8/1988 | Keith et al. |
| 4,765,983 A | 8/1988 | Takayanagi et al. |
| 4,784,858 A | 11/1988 | Ventouras |
| 4,857,336 A | 8/1989 | Khanna et al. |
| 4,867,970 A | 9/1989 | Newsham et al. |
| 4,876,092 A | 10/1989 | Mizobuchi et al. |
| 4,889,720 A | 12/1989 | Konishi |
| 4,894,232 A | 1/1990 | Reul et al. |
| 4,900,552 A | 2/1990 | Sanvordeker et al. |
| 4,900,554 A | 2/1990 | Yanagibashi et al. |
| 4,906,463 A | 3/1990 | Cleary et al. |
| 4,915,948 A | 4/1990 | Gallopo et al. |
| 4,990,339 A | 2/1991 | Scholl et al. |
| 5,047,244 A | 9/1991 | Sanvordeker et al. |
| 5,059,189 A | 10/1991 | Cilento et al. |
| 5,064,654 A | 11/1991 | Berner et al. |
| 5,081,157 A | 1/1992 | Pomerantz |
| 5,081,158 A | 1/1992 | Pomerantz |
| 5,116,621 A | 5/1992 | Oji et al. |
| 5,137,729 A | 8/1992 | Kuroya et al. |
| 5,149,538 A | 9/1992 | Granger et al. |
| 5,166,233 A | 11/1992 | Kuroya et al. |
| 5,192,802 A | 3/1993 | Rencher |
| 5,196,202 A | 3/1993 | Konishi |
| 5,202,128 A | 4/1993 | Morella et al. |
| 5,236,714 A | 8/1993 | Lee et al. |

(Continued)

FOREIGN PATENT DOCUMENTS

AU 741362 B2 11/2001
CA 2169729 A1 2/1995

(Continued)

OTHER PUBLICATIONS

1999 Refresher Course Lecture and Clinical Update Index, retrieved online at http://anesthesia.stanford.edu/RCLS.pdf (1999).
Actiq Product Label, Approved Sep. 24, 2004 (Drug first approved Nov. 4, 1998); 31 pages.
BioDelivery Sciences International Press Release Dated Nov. 1, 2005, 2 pages.
BioDelivery Sciences International Press Release, Dated Apr. 24, 2006, 2 pages.
BioDelivery Sciences International Press Release, Dated Mar. 7, 2005, 2 pages.
BioDelivery Sciences International Press Release, Dated May 22, 2006, 2 pages.
BioDelivery Sciences International, The Wall Street Analyst Forum, Nov. 29, 2005.

(Continued)

*Primary Examiner* — David J Blanchard
*Assistant Examiner* — Daniel F Coughlin
(74) *Attorney, Agent, or Firm* — Womble Bond Dickinson (US) LLP; Danielle L. Herritt (57) ABSTRACT

Provided herein are methods for treating chronic pain by administering low doses of buprenorphine twice daily (or once daily) via a transmucosal drug delivery device. The methods and devices efficiently treat chronic pain without significant side effects.

22 Claims, 3 Drawing Sheets

(56) References Cited

U.S. PATENT DOCUMENTS

| | | |
|---|---|---|
| 5,254,345 A | 10/1993 | Pogany et al. |
| 5,254,346 A | 10/1993 | Tucker et al. |
| 5,288,497 A | 2/1994 | Stanley et al. |
| 5,288,498 A | 2/1994 | Stanley et al. |
| 5,298,256 A | 3/1994 | Flockhart et al. |
| 5,298,258 A | 3/1994 | Akemi et al. |
| 5,314,915 A | 5/1994 | Rencher |
| 5,332,576 A | 7/1994 | Mantelle |
| 5,346,701 A | 9/1994 | Heiber et al. |
| 5,436,701 A | 7/1995 | Shimojo et al. |
| 5,462,749 A | 10/1995 | Rencher |
| 5,466,465 A | 11/1995 | Royds et al. |
| 5,505,956 A | 4/1996 | Kim et al. |
| 5,516,523 A | 5/1996 | Heiber et al. |
| 5,540,930 A | 7/1996 | Guy et al. |
| 5,599,554 A | 2/1997 | Majeti |
| 5,603,947 A | 2/1997 | Wong et al. |
| 5,679,714 A | 10/1997 | Weg |
| 5,700,478 A | 12/1997 | Biegajski et al. |
| 5,723,143 A | 3/1998 | Jacques et al. |
| 5,750,136 A | 5/1998 | Scholz et al. |
| 5,780,047 A | 7/1998 | Kamiya et al. |
| 5,785,989 A | 7/1998 | Stanley et al. |
| 5,800,832 A | 9/1998 | Tapolsky et al. |
| 5,849,322 A | 12/1998 | Ebert et al. |
| 5,853,760 A | 12/1998 | Cremer |
| 5,855,908 A | 1/1999 | Stanley et al. |
| 5,900,247 A | 5/1999 | Rault et al. |
| 5,948,430 A | 9/1999 | Zerbe et al. |
| 5,985,317 A | 11/1999 | Venkateshwaran et al. |
| 6,159,498 A | 12/2000 | Tapolsky et al. |
| 6,177,096 B1 | 1/2001 | Zerbe et al. |
| 6,200,604 B1 | 3/2001 | Pather et al. |
| 6,228,863 B1 | 5/2001 | Palermo et al. |
| 6,255,502 B1 | 7/2001 | Penkler et al. |
| 6,264,980 B1 | 7/2001 | Hille |
| 6,264,981 B1 | 7/2001 | Zhang et al. |
| 6,277,384 B1 | 8/2001 | Kaiko et al. |
| 6,284,262 B1 | 9/2001 | Place |
| 6,375,957 B1 | 4/2002 | Kaiko et al. |
| 6,475,494 B2 | 11/2002 | Kaiko et al. |
| 6,552,024 B1 | 4/2003 | Chen et al. |
| 6,562,363 B1 | 5/2003 | Mantelle et al. |
| 6,582,724 B2 | 6/2003 | Hsu et al. |
| 6,585,997 B2 | 7/2003 | Moro et al. |
| 6,592,887 B2 | 7/2003 | Zerbe et al. |
| 6,696,066 B2 | 2/2004 | Kaiko et al. |
| 6,696,088 B2 | 2/2004 | Oshlack et al. |
| 6,716,449 B2 | 4/2004 | Oshlack et al. |
| 6,719,997 B2 | 4/2004 | Hsu et al. |
| 6,759,059 B1 | 7/2004 | Pettersson et al. |
| 6,780,504 B2 | 8/2004 | Rupprecht et al. |
| 6,835,392 B2 | 12/2004 | Hsu et al. |
| 6,969,374 B2 | 11/2005 | Krantz et al. |
| 7,144,587 B2 | 12/2006 | Oshlack et al. |
| 7,157,103 B2 | 1/2007 | Sackler |
| 7,172,767 B2 | 2/2007 | Kaiko et al. |
| 7,579,019 B2 | 8/2009 | Tapolsky et al. |
| 8,147,866 B2 | 4/2012 | Finn et al. |
| 8,703,177 B2 | 4/2014 | Finn et al. |
| 2002/0034554 A1 | 3/2002 | Hsu et al. |
| 2002/0058068 A1 | 5/2002 | Houze et al. |
| 2002/0142036 A1 | 10/2002 | Rupprecht et al. |
| 2002/0160043 A1 | 10/2002 | Coleman |
| 2003/0044446 A1 | 3/2003 | Moro et al. |
| 2003/0104041 A1 | 6/2003 | Hsu et al. |
| 2003/0124176 A1 | 7/2003 | Hsu et al. |
| 2003/0161870 A1 | 8/2003 | Hsu et al. |
| 2003/0170195 A1 | 9/2003 | Houze et al. |
| 2003/0194420 A1 | 10/2003 | Holl et al. |
| 2004/0018241 A1 | 1/2004 | Houze et al. |
| 2004/0024003 A1 | 2/2004 | Asmussen et al. |
| 2004/0033255 A1 | 2/2004 | Baker et al. |
| 2004/0110781 A1 | 6/2004 | Harmon et al. |
| 2004/0126323 A1 | 7/2004 | Shevchuk et al. |
| 2004/0126416 A1 | 7/2004 | Reidenberg et al. |
| 2004/0151774 A1 | 8/2004 | Pauletti et al. |
| 2004/0180080 A1 | 9/2004 | Furusawa et al. |
| 2004/0191301 A1 | 9/2004 | Van Duren |
| 2004/0213828 A1 | 10/2004 | Smith |
| 2004/0219195 A1 | 11/2004 | Hart et al. |
| 2004/0219196 A1 | 11/2004 | Hart et al. |
| 2004/0220262 A1 | 11/2004 | Hsu et al. |
| 2004/0241218 A1 | 12/2004 | Tavares et al. |
| 2005/0002997 A1 | 1/2005 | Howard et al. |
| 2005/0013845 A1 | 1/2005 | Warren et al. |
| 2005/0037055 A1 | 2/2005 | Yang et al. |
| 2005/0042281 A1 | 2/2005 | Singh et al. |
| 2005/0048102 A1 | 3/2005 | Tapolsky et al. |
| 2005/0074487 A1 | 4/2005 | Hsu et al. |
| 2005/0085440 A1 | 4/2005 | Birch et al. |
| 2005/0169977 A1 | 8/2005 | Kanios et al. |
| 2005/0222135 A1 | 10/2005 | Buschmann et al. |
| 2006/0003008 A1 | 1/2006 | Gibson et al. |
| 2006/0051413 A1 | 3/2006 | Chow et al. |
| 2006/0069086 A1 | 3/2006 | Michalow |
| 2006/0073102 A1 | 4/2006 | Huaihung et al. |
| 2006/0073189 A1 | 4/2006 | Pinney et al. |
| 2006/0130828 A1 | 6/2006 | Sexton et al. |
| 2007/0148097 A1* | 6/2007 | Finn .............. A61K 9/0014 424/10.2 |
| 2007/0149731 A1 | 6/2007 | Myers |
| 2007/0207192 A1 | 9/2007 | Holl et al. |
| 2008/0160068 A1 | 7/2008 | Hille et al. |
| 2008/0254105 A1 | 10/2008 | Tapolsky et al. |
| 2008/0317828 A1 | 12/2008 | Furusawa et al. |
| 2009/0270438 A1 | 10/2009 | Booles et al. |
| 2010/0003308 A1 | 1/2010 | Tapolsky et al. |
| 2010/0010031 A1* | 1/2010 | Yum, II ............ A61K 9/0056 514/282 |
| 2010/0015183 A1 | 1/2010 | Finn et al. |
| 2010/0168147 A1 | 7/2010 | Chapleo et al. |
| 2011/0033541 A1 | 2/2011 | Myers et al. |
| 2011/0033542 A1 | 2/2011 | Myers et al. |
| 2011/0189259 A1 | 8/2011 | Vasisht et al. |
| 2011/0262522 A1* | 10/2011 | Finn et al. ................ 424/444 |
| 2012/0027839 A1 | 2/2012 | Tapolsky et al. |
| 2013/0045268 A1 | 2/2013 | Finn et al. |
| 2014/0178440 A1 | 6/2014 | Finn et al. |
| 2015/0246002 A1 | 9/2015 | Finn et al. |
| 2015/0366793 A1 | 12/2015 | Finn et al. |
| 2016/0095821 A1 | 4/2016 | Finn et al. |
| 2016/0101061 A1 | 4/2016 | Tapolsky et al. |
| 2016/0310409 A1 | 10/2016 | Finn et al. |

FOREIGN PATENT DOCUMENTS

| | | |
|---|---|---|
| CN | 101511337 A | 8/2009 |
| EP | 0 050 480 A2 | 4/1982 |
| EP | 069600 A2 | 1/1983 |
| EP | 0159604 A2 | 10/1985 |
| EP | 0 250 187 A2 | 12/1987 |
| EP | 0 262 422 A1 | 4/1988 |
| EP | 0 275 550 A1 | 7/1988 |
| EP | 0 381 194 A2 | 8/1990 |
| EP | 0 654 261 A1 | 5/1995 |
| EP | 0 781 546 A1 | 7/1997 |
| EP | 1021204 A2 | 7/2000 |
| EP | 1105104 A1 | 6/2001 |
| EP | 1201233 A1 | 5/2002 |
| EP | 1642579 A1 | 4/2006 |
| FR | 2497098 A1 | 7/1982 |
| FR | 2582942 A1 | 12/1986 |
| GB | 981372 A | 1/1965 |
| GB | 2108841 A | 5/1983 |
| JP | 56-100714 A | 8/1981 |
| JP | 58-079916 A | 5/1983 |
| JP | 60-116630 A | 6/1985 |
| JP | 61-280423 A | 12/1986 |
| JP | 62-022713 A | 1/1987 |
| JP | 62-056420 A | 3/1987 |
| JP | 62-135417 A | 6/1987 |
| JP | 62-178513 A | 8/1987 |
| JP | 63-060924 A | 3/1988 |

(56) References Cited

FOREIGN PATENT DOCUMENTS

| | | |
|---|---|---|
| JP | 63-160649 A | 7/1988 |
| JP | 63-310818 A | 12/1988 |
| JP | 64-071812 | 3/1989 |
| JP | 1-226823 A | 9/1989 |
| JP | 3-246220 A | 11/1991 |
| JP | 4-059723 A | 2/1992 |
| JP | 9-504810 | 5/1997 |
| JP | 64-090121 | 4/1999 |
| JP | 2001-506640 A | 5/2001 |
| JP | 2001-508037 A | 6/2001 |
| JP | 2002-526403 A | 8/2002 |
| JP | 2005-504763 A | 2/2005 |
| WO | WO-1994/18925 A1 | 9/1994 |
| WO | WO-1995/05416 A2 | 2/1995 |
| WO | WO-1995/25544 A1 | 9/1995 |
| WO | WO-1998/26780 A2 | 6/1998 |
| WO | WO-1999/15210 A2 | 4/1999 |
| WO | WO-2000/19987 A1 | 4/2000 |
| WO | 2000/042992 A2 | 7/2000 |
| WO | WO-2001/30288 A1 | 5/2001 |
| WO | WO-2001/43728 A1 | 6/2001 |
| WO | WO-2001/58447 A1 | 8/2001 |
| WO | WO-2001/85257 A2 | 11/2001 |
| WO | WO-2002/092060 A1 | 11/2002 |
| WO | WO-2003/013525 A1 | 2/2003 |
| WO | WO-2003/013538 A1 | 2/2003 |
| WO | WO-2003/070191 A2 | 8/2003 |
| WO | WO-2004/017941 A2 | 3/2004 |
| WO | WO-2005/016321 A1 | 2/2005 |
| WO | WO-2005/044243 A2 | 5/2005 |
| WO | WO-2005/055981 A2 | 6/2005 |
| WO | WO-2005/081825 A2 | 9/2005 |
| WO | WO-2007/007059 A1 | 1/2007 |
| WO | WO-2007/070632 A2 | 6/2007 |
| WO | WO 2008011194 A2 * | 1/2008 |
| WO | WO-2008/025791 A1 | 3/2008 |
| WO | WO-2008/040534 A2 | 4/2008 |
| WO | WO-2008/047163 A1 | 4/2008 |
| WO | WO-2008/100434 A1 | 8/2008 |
| WO | 2011/017484 A2 | 2/2011 |

OTHER PUBLICATIONS

Durfee et al., "Fentanyl Effervescent Buccal Tablets," American Journal of Drug Delivery, 2006, 4(1): 1-5.
Extended European Search Report for European Patent Application No. 12860757.9 dated Jan. 20, 2016.
Fentora Product Label, Approved Sep. 25, 2006 (Drug first approved Sep. 25, 2006); 41 pages.
Fine et al., "A Review of Oral Transmucosal Fentanyl Citrate: Potent, Rapid and Noninvasive Opioid Analgesia," Journal of Palliative Medicine, 1998, 1(1): 55-63.
Garrett et al., "Pharmacokinetics of morphine and its surrogates VI: Bioanalysis, solvokinetics, solubility, pKa values and protein binding of buprenorphine," Journal of Pharmaceutical Sciences, 1985, 74(5), pp. 515-524.
Guo J.-H. and Cooklock, K.M., "*Bioadhesive polymer buccal patches for buprenorphine controlled delivery: solubility consideration*" Drug Development and Industrial Pharmacy 21:2013-2019 (1995).
International Preliminary Report on Patentability for related PCT Application No. PCT/US2009/048325 dated Jan. 5, 2011.
International Search Report and Written Opinion for International Application No. PCT/US2007/016634, dated Mar. 17, 2008. 14 pages.
International Search Report and Written Opinion for PCT/US2012/071330 dated Feb. 22, 2013.
International Search Report for Application No. PCT/US2006/047686, dated Aug. 13, 2007.
International Search Report for related PCT Application No. PCT/US2009/048325 dated Aug. 5, 2009.

Katz, Nathaniel, P. et al., "Anesthetic and Life Support Drugs Advisory Committee, Meeting, Wednesday, Jan. 2002," retrieved online at http://www.fda.gov/ohrms/dockets/ac/02/transcripts/3820t1.pdf (2002).
Lahmeyer, H.W. et al., "Pentazocine-naloxone: an 'abuse proof' drug can be abused," *J. Clin. Psychopharmacol.*, vol. 6(6):389-390 (1986).
McQuinn R.L. et al., "Sustained oral mucosal delivery in human volunteers of buprenorphine from a thin non-eroding mucoadhesive polymeric disk" Journal of Controlled Release 34:243-250 (1995).
Partial European Search Report for European Patent Application No. 12860757.9 dated Sep. 15, 2015.
Pather et al. "Enhanced Buccal Delivery of Fentanyl Using the OraVescent Drug Delivery System," Drug Delivery Tech. vol. 1, No. 1, Oct. 2001. Downloaded from www.drugdeliverytech.com, last accessed Dec. 20, 2010. 6 pages.
Robertson et al., "PK-PD modeling of buprenorphine in cats: intravenous and oral transmucosal administration," J. Vet. Pharmacol. Therap., 2005, 28, 453-460.
Roy et al., "Transdermal delivery of buprenorphine through cadaver skin," Journal of Pharmaceutical Sciences, 1994, 83(2), pp. 126-130.
Screenshots From www.fentora.com; pages downloaded Jul. 20, 2007, 6 pages.
Shi et al., "Studies on the Transoral Mucosal Absorption of Fentanyl", Chin. Pharm. J., 2005, vol. 40, No. 13, pp. 996-998.
Shojaei, A. et al., "Buccal Mucosa As a Route for System Drug Delivery: A Review," Journal of Pharmacy and Pharmaceutical Sciences (ualberta.ca/~csps), 1998, 1(1): 15-30.
Streisand et al. "Buccal Absorption of Fentanyl is pH dependent in Dogs," Anesthesiology, 82(3): 759-64 (1995).
The Merck Manual, http://www.merck.com/mmhe/sec06/ch078a.html?qt=pain&alt=sh, obtained online on Apr. 9, 2009.
U.S. Department of Justice, "Intelligence Bulletin, Buprenorphine: Potential for Abuse," retrieved online at http://www.usdoj.gov/ndic/pubs10/10123/10123p.pdf; Sep. 2004.
Webster's New World Dictionary (1988), V. Neufeldt ed. and D.B. Guralink ed., Prentice Hall: New York 3rd. College Ed., p. 505.
Webster, L. (2006) Expert Opinion 15(11):1469-1473.
Weinberg, S. et al., "Sublingual absorption of selected opioid analgesics" Clin. Pharmacol. Ther. 44:335-342 (1988).
Written Opinion for related PCT Application No. PCT/US2009/048325 dated Aug. 5, 2009.
U.S. Appl. No. 14/829,811, filed Aug. 19, 2015, Published, 2016-0101061-A1, Apr. 14, 2016.
U.S. Appl. No. 15/198,961, filed Jun. 30, 2016, Pending.
U.S. Appl. No. 15/212,912, filed Jul. 18, 2016, Pending.
U.S. Appl. No. 15/213,051, filed Jul. 18, 2016, Pending.
U.S. Appl. No. 15/213,137, filed Jul. 18, 2016, Pending.
U.S. Appl. No. 11/639,408, filed Dec. 13, 2006, Granted, U.S. Pat. No. 9,522,188, Dec. 20, 2016.
U.S. Appl. No. 15/379,646, filed Dec. 15, 2016, Pending.
U.S. Appl. No. 15/198,961, filed Jun. 30, 2016, Granted, U.S. Pat. No. 9,597,288, Mar. 21, 2017.
U.S. Appl. No. 15/212,912, filed Jul. 18, 2016, Published, 2016-0324768-A1, Nov. 10, 2016.
U.S. Appl. No. 15/429,385, filed Feb. 10, 2017, Pending.
U.S. Appl. No. 15/213,051, filed Jul. 18, 2016, Published, 2016-0339016-A1, Nov. 24, 2016.
U.S. Appl. No. 15/213,137, filed Jul. 18, 2016, Published, 2016-0324849-A1, Nov. 10, 2016.
U.S. Appl. No. 14/875,107, filed Oct. 5, 2015, Pending.
"Defendant's initial invalidity contentions" United States District Court for the District of Delaware, C.A. No. 16-175-GMS, dated Oct. 28, 2016, 54 pages.
Chiang et al., "Pharmacokinetics of the combination tablet of buprenorphine and naloxone," Drug and Alcohol Dependence 70 (2003) S39-S47.
Das et al., "Development of Mucoadhesive Dosage Forms of Buprenorphine for Sublingual Drug Delivery," Drug Delivery, pp. 89-95, 2004.
Hiroshima Ishikai Dayori, Jun. 15, 2011, issue 542, pp. 2-5.

(56) References Cited

OTHER PUBLICATIONS

Meschia, et al., "Effect of Hormone Replacement Therapy and Calcitonin on Bone Mass in Postmenopausal Women" Eur J Obstet Gynecol Reprod Biol. Oct. 23, 1992;47(1):53-7.
Package Insert of sustained-release transdermal analgesic formulation "Norspan Tape 5 mg, 10 mg, 20 mg", Feb. 2011, pp. 1-4.

* cited by examiner

TRANSMUCOSAL DRUG DELIVERY DEVICES FOR USE IN CHRONIC PAIN RELIEF

RELATED APPLICATIONS

This application claims priority to U.S. Provisional Application No. 61/578,755, filed Dec. 21, 2011. The entire contents of this application are incorporated herein by reference.

This application is related to U.S. patent application Ser. No. 08/734,519, filed on Oct. 18, 1996, now U.S. Pat. No. 5,800,832, issued Sep. 1, 1998; U.S. patent application Ser. No. 09/144,827, filed on Sep. 1, 1998, now U.S. Pat. No. 6,159,498, issued on Dec. 12, 2000; U.S. patent application Ser. No. 11/069,089, filed on Mar. 1, 2005, now U.S. Pat. No. 7,579,019, issued on Aug. 25, 2009; U.S. patent application Ser. No. 11/639,408, filed on Dec. 13, 2006; U.S. patent application Ser. No. 11/817,915, filed on Sep. 6, 2007; U.S. patent application Ser. No. 13/834,306, filed on Jul. 15, 2011, now U.S. Pat. No. 8,147,866, issued on Apr. 3, 2012; U.S. patent application Ser. No. 13/590,094, filed on Aug. 20, 2012, the entire contents of which are incorporated herein by reference.

BACKGROUND

Chronic pain is pain that persists beyond the expected healing time, if resulting from injury, and can progress from a bothersome nuisance to a profound affliction. Chronic pain can cause a marked alteration in behavior with depression and anxiety, restriction in daily activities and excessive use of medication and medical services in an afflicted individual. The treatment of chronic pain is difficult, often inadequate and associated with high economic and psychological cost.

Buprenorphine is a partial μ-opiate receptor agonist, an ORL1/nociceptin receptor agonist with high affinity and a slow dissociation rate and a κ-opiate receptor antagonist.

Buprenorphine is metabolized by the liver, via the CYP3A4 isozyme of the cytochrome P450 enzyme system, into norbuprenorphine (by N-dealkylation) and other metabolites. Buprenorphine has a low oral bioavailability due to very high first-pass metabolism.

Buprenorphine is an analgesic, available commercially as Temgesic® 0.2 mg sublingual tablets, and as Buprenex® in a 0.3 mg/ml parenteral formulation. Buprenorphine is also available as a sublingual preparation (Subutex®) and as a sublingual abuse-resistant formulation with naloxone (Suboxone®). The FDA approved Suboxone/Subutex in 2002 as a treatment of opioid dependence. Sublingual buprenorphine has been used for opioid detoxification and maintenance.

A recent open-label study used sublingual buprenorphine (Suboxone®) for the treatment of chronic pain to those chronic opioid users (Malinoff et al., 2005, *American Journal of Therapeutics* 12, 379-384). Patients were treated with daily buprenorphine doses that ranged from 2-20 mg (mean 8 mg). The treatment lasted from 2.4 months to 16.6 months (mean 8.8 months). The article reports that patients experienced improvement in their condition and reported a decrease in their sensation of pain.

Still, effective methods for treating chronic pain that are not associated with adverse effects are needed, especially to those opioid naive or opioid experienced patients.

SUMMARY OF THE INVENTION

The present teachings provide methods for treating chronic pain by administering low doses of buprenorphine twice daily (or once daily) via a mucoadhesive bioerodable drug delivery device. The methods and devices efficiently treat chronic pain without significant side effects, for example, less than 15% (preferably less than 10%, more preferably less than 5%) patients experience constipation.

The devices comprise about 100 μg to 0.9 mg buprenorphine, and provide steady-state $C_{max}$ of plasma buprenorphine concentration in a range between about 0.1 and about 1.2 ng/mL, such that the subject is treated for chronic pain.

In one embodiment, the buprenorphine delivery device comprises a bioerodable mucoadhesive layer comprising a therapeutically effective amount of buprenorphine disposed in a buffered polymeric diffusion environment, wherein the polymeric diffusion environment is a buffered environment having a pH of between about 4 and about 6. In another embodiment, the buprenorphine delivery device further comprises a bather layer comprising a polymeric barrier environment disposed adjacent to the mucoadhesive layer to provide a unidirectional gradient upon application to a mucosal surface for the rapid and efficient delivery of buprenorphine, wherein the unidirectional gradient delivers buprenorphine across the buffered polymeric diffusion environment upon application to the mucosal surface. In still another embodiment, the device comprises a mucoadhesive layer comprising an effective amount of buprenorphine buffered to a pH of between about 4.0 and about 6.0, and a backing layer buffered to a pH between about 4.0 and about 4.8.

In one embodiment, the device comprises about 120 μg to 0.9 mg buprenorphine.

The methods and devices disclosed therein can be used to treat a subject with chronic low back pain, such as moderate to severe chronic low back pain, or a subject with neuropathic pain or osteoarthritic pain.

DETAILED DESCRIPTION OF THE INVENTION

The present invention provides methods of treating chronic pain with low doses of buprenorphine. The present method of treating pain is also associated with lack of significant opioid adverse effects. For example, the subject is treated without experiencing any severe common opioid adverse effects. Or, the subject is treated experiencing mild or moderate common opioid adverse effects, or no common opioid adverse effects.

The present invention also provides effective chronic pain relief with twice daily administration of buprenorphine. The present invention is based, at least in part, on the surprising discovery that a transmucosal drug delivery device containing low doses of buprenorphine can be administered twice daily to opioid experienced subjects for effective management and relief of chronic pain, such as chronic low back pain. The present invention is also based on the discovery that this therapy does not result in substantial side effects associated with opioids, such as constipation and nausea.

Definitions

The following definitions are provided as guidance as to the meaning of certain terms used herein.

As used herein, the articles "a" and "an" mean "one or more" or "at least one," unless otherwise indicated. That is, reference to any element of the present invention by the indefinite article "a" or "an" does not exclude the possibility that more than one of the element is present.

As used herein, the term "acute pain" refers to pain characterized by a short duration, e.g., three to six months. Acute pain is typically associated with tissue damage, and manifests in ways that can be easily described and observed. It can, for example, cause sweating or increased heart rate. Acute pain can also increase over time, and/or occur intermittently.

As used herein, the term "bioavailability" is as defined in 21 CFR Section 320.1 and refers to the rate and extent to which the active ingredient or active moiety is absorbed from a drug product and becomes available at the site of action. The term "bioavailability", "absolute bioavailability" or "total bioavailability" refers to the total bioavailability including amounts that are absorbed through the oral mucosal membrane (i.e., transmucosally) and through the GI mucosa of the lower GI tract. In some embodiments, the transmucosal drug delivery devices of the present invention provide bioavailability of buprenorphine of between 65% and 85%. In some embodiments, the bioavailability of buprenorphine is 80%.

As used herein, the term "bioequivalence" or "bioequivalent" is as defined in 21 CFR Section 320.1, and means the absence of a significant difference in the rate and extent to which the active ingredient or active moiety in pharmaceutical equivalents or pharmaceutical alternatives becomes available at the site of drug action when administered at the same molar dose under similar conditions in an appropriately designed study. The pharmacokinetic parameters $C_{max}$ and AUC for bioequivalent actives fall within the 80%-125% range of each other.

As used herein, the term "chronic pain" refers to pain which persists beyond the usual recovery period for an injury or illness. In one embodiment, chronic pain is the pain that lasts longer than one week. Chronic pain can be constant or intermittent. Common causes of chronic pain include, but are not limited to, arthritis, cancer, Reflex Sympathetic Dystrophy Syndrome (RSDS), repetitive stress injuries, shingles, headaches, fibromyalgia, and diabetic neuropathy.

As used herein, the term "chronic low back pain" refers to a muscoskeletal disorder, wherein the subject experiences pain in the lumbar, or low back region for at least 12 weeks. In a specific embodiment, a subject experiences chronic low back pain for at least 3 months.

As used herein, the term "moderate to severe chronic low back pain" refers to the chronic low back pain characterized, e.g., by pain intensity of ≥5 on an 11-point Numerical Rating Scale (NRS, wherein 0 represents no pain and 10 represents the worst pain imaginable).

As used herein, the term "neuropathic pain" refers to a complex, chronic pain that usually is accompanied by tissue injury and results from lesions or diseases affecting the somatosensory system. With neuropathic pain, the nerve fibers themselves may be damaged, dysfunctional or injured. These damaged nerve fibers send incorrect signals to other pain centers. The impact of nerve fiber injury includes a change in nerve function both at the site of injury and areas around the injury.

As used herein, the term "osteoarthritic pain" refers to pain resulting from osteoarthritis, a degenerative joint disease and the most common type of arthritis. It is associated with the degradation and loss of a cartilage that covers and cushions the ends of bones in normal joints. Osteoarthritis causes the cartilage in a joint to become stiff and lose its elasticity, making it more susceptible to damage. Over time, the cartilage may wear away in some areas, greatly decreasing its ability to act as a shock absorber. As the cartilage wears away, tendons and ligaments stretch, causing pain. If the condition worsens, the bones could rub against each other, causing even more pain and loss of movement.

As used herein, unless indicated otherwise, the term "buprenorphine", includes any pharmaceutically acceptable form of buprenorphine, including, but not limited to, salts, esters, and prodrugs thereof. As used herein, the term "buprenorphine derivative" refers to compounds having similar structure and function to buprenorphine. In some embodiments, buprenorphine derivatives include those of the following formula:

or pharmaceutically acceptable salts or esters thereof, wherein is a double or single bond; $R_3$ is selected from a —$C_{1-4}$ alkyl group or a cycloalkyl-substituted-$C_{1-4}$ alkyl group; $R_4$ is selected from a —$C_{1-4}$ alkyl; $R_5$ is —OH, or taken together, $R_4$ and $R_5$ form a =O group; and $R_6$ is selected from —H or a —$C_{1-4}$ alkyl group.

Buprenorphine derivatives include, but are not limited to, etorphine and diprenorphine. General buprenorphine derivatives are described in International Application Publication No. WO 2008/011194, which is hereby incorporated by reference.

As used herein, unless indicated otherwise, the term "naloxone" includes any pharmaceutically acceptable form of naloxone, including, but not limited to, salts, esters, and prodrugs thereof.

As used herein, "non-parenteral" refers to modes of administration other than by direct systemic delivery of the medicament. As such, "non-parenteral" excludes the use of intravenous (IV) injection, intramuscular (IM) injection, Intraperitoneal (IP) injection, subcutaneous (SC) injection, etc. for administration of the medicament and includes transdermal, oral transmucosal administration, and administration via the GI tract, generally.

As used herein, the term "mucoadhesive layer" or "polymeric diffusion environment" refers to an environment capable of allowing flux of a medicament to a mucosal surface upon creation of a gradient by adhesion to a mucosal surface. The flux of a transported medicament is proportionally related to the diffusivity of the environment which can be manipulated by, e.g., adjusting the pH, taking into account the ionic nature of the medicament and/or the ionic nature of the polymer or polymers included in the environment.

As used herein, the term "backing layer" or "barrier environment" or "non-adhesive polymeric environment" refers to an environment in the form of, e.g., a layer or coating or barrier layer, capable of slowing, or reducing flux of a medicament from the mucoadhesive layer into the oral cavity. In some embodiments, the backing layer may contain a second medicament intended for dissolution in the saliva. In such cases, the pH of the backing layer is adjusted, such that it impedes flux of the medicament toward the mucoadhesive layer where transmucosal absorption may occur. As used herein, the term "unidirectional gradient" refers to a gradient which allows for the flux of a medicament (e.g., buprenorphine) through the device, e.g., through a polymeric diffusion environment, in substantially one direction, e.g., to the oral mucosa of a subject. For example, the polymeric diffusion environment may be a mucoadhesive polymeric diffusion environment in the form of a layer or film disposed adjacent to a backing layer or film. Upon oral mucosal application, a gradient is created between the mucoadhesive polymeric diffusion environment and the mucosa, and the medicament flows from the mucoadhesive polymeric diffusion environment, substantially in one direction towards the mucosa, until the backing layer dissolves.

As used herein, "treating" or "treatment" of a subject includes the administration of a drug to a subject with the purpose of preventing, curing, healing, alleviating, relieving, altering, remedying, ameliorating, improving, stabilizing or affecting a disease or disorder, or a symptom of a disease or disorder (e.g., to alleviate pain).

The term "subject" refers to living organisms such as humans, dogs, cats, and other mammals. Administration of the medicaments included in the devices of the present invention can be carried out at dosages and for periods of time effective for treatment of a subject. In some embodiments, the subject is a human. In some embodiments, the pharmacokinetic profiles of the devices of the present invention are similar for male and female subjects.

An "effective amount" of a drug necessary to achieve a therapeutic effect may vary according to factors such as the age, sex, and weight of the subject. Dosage regimens can be adjusted to provide the optimum therapeutic response. For example, the dosage may be administered once daily, or may be divided into two individual dosages for twice daily administration. The dose may also be proportionally reduced as indicated by the exigencies of the therapeutic situation.

The term "transmucosal," as used herein, refers to any route of administration via a mucosal membrane. Examples include, but are not limited to, buccal, sublingual, nasal, vaginal, and rectal. In one embodiment, the administration is buccal. In one embodiment, the administration is sublingual. As used herein, the term "direct transmucosal" refers to mucosal administration via the oral mucosa, e.g., buccal and/or sublingual.

As used herein, the term "water erodable" or "at least partially water erodable" refers to a substance that exhibits a water erodability ranging from negligible to completely water erodable. The substance may readily dissolve in water or may only partially dissolve in water with difficulty over a long period of time. Furthermore, the substance may exhibit a differing erodability in body fluids compared with water because of the more complex nature of body fluids. For example, a substance that is negligibly erodable in water may show an erodability in body fluids that is slight to moderate. However, in other instances, the erodability in water and body fluid may be approximately the same.

As used herein, "addiction therapy" as related to a subject includes the administration of a drug to a subject with the purpose of reducing the cravings for the addictive substance.

As used herein, the term "opioid tolerance" refers to the phenomenon in which a subject is less susceptible to the effect of an opioid drug as a consequence of its prior administration. "Acute tolerance" describes tolerance that develops very rapidly following either a single dose or a few doses of opioids given over a short period of time. "Chronic tolerance" describes the observation that opioid administration over a longer period of time produces reduced effects. Associative tolerance is best expressed with low doses of opioids at long interdose intervals and is readily modified by behavioral or environmental interventions. Nonassociative tolerance is best expressed with high doses of drugs at short interdose intervals and is not modified by behavioral or environmental interventions.

As used herein, the term "opioid tolerant subject" refers to a subject currently receiving opioid therapy. In one embodiment, the subject is taking >60 mg oral morphine/day or equianalgesic dose of another opioid for 1 week or longer, as specified in the Table 1 below.

TABLE 1

| Opioid | Approximate Equianalgesic Oral Doses |
|---|---|
| Morphine | 60 mg |
| Tramadol | 300 mg |
| Hydromorphone | 12 mg |
| Oxycodone | 30 mg |
| Hydrocodone | 30 mg |
| Oxymorphone | 20 mg |
| Codeine | 400 mg |

As used herein, the term "opioid experienced subject" refers to a subject currently receiving opioid therapy. In one embodiment, the subject's daily use of opioids does not exceed the daily doses of opioids as specified in the Table 1 above.

As used herein, the term "opioid naive subject" refers to a subject who is not currently receiving opioid therapy. In one embodiment, the subject has not been exposed to opioids for 1 week or longer.

As used herein, the term "abusive" or "abusive manner" refers to uses of the devices beyond oral transmucosal administration such as by extracting the drug and injecting or snorting.

As used herein, the term "low dose of buprenorphine" refers to the daily dose less than 1.8 mg (e.g., about 200 µg to about 1800 µg, or about 240 µg to 1800 µg) of buprenorphine.

As used herein, the term "steady-state plasma concentration" refers to the state, wherein the fluctuation in plasma drug concentrations are the same or similar after each dose. The term "steady-state $C_{max}$ of plasma buprenorphine concentration" refers to the state, wherein the post dose maximum plasma concentration of buprenorphine does not differ from one dose to another. The term "steady-state $C_{min}$ of plasma buprenorphine concentration" refers to the state, wherein the post-dose minimum plasma concentration of buprenorphine does not differ from one dose to another. In one embodiment, the devices used in the present invention provide steady-state $C_{max}$ of plasma buprenorphine concentration in a range between about 0.1 and about 1.0 ng/mL. In another embodiment, the devices used in the present invention provide steady-state $C_{max}$ of plasma buprenorphine concentration in a range between about 0.1 and about 0.5 ng/mL.

As used herein, the term "common opioid adverse effects" refers to adverse effects commonly experienced by the subjects taking opioid analgesics. These common opioid adverse effects include, among others, headache, constipation, nausea or vomiting, pruritus, somnolence or cognitive impairment, dry mouth, tolerance or dependence and urinary retention.

The term "mild common opioid adverse effects" refers to adverse effects that do not require a special treatment and do not interfere with the subject's daily activities. The term "moderate common opioid adverse effects" refers to adverse effects that introduce a low level of inconvenience or concern to the subjects and could interfere with daily activities, but are usually ameliorated by simple therapeutic measures. The term "severe common opioid adverse effects" refers to adverse effects that interrupt usual daily activity and typically require systemic drug therapy or other treatment.

The term "significant constipation" refers to chronic or severe constipation associated with the continuous use of morphine or other opioids.

The term "significant nausea" refers to a severe condition of nausea that is commonly known in the art. In some embodiments, the term "significant nausea" is defined with a visual analog scale (VAS) score of greater than or equal to 25 mm on a 0 to 100 mm scale.

As used herein, the term "disposed" refers to the uniform or non-uniform distribution of an element within another.

Pain Management

Certain aspects of the present invention include methods for providing pain management and/or relief to a subject in need thereof. The pain can be any pain known in the art, caused by any disease, disorder, condition and/or circumstance and can be chronic pain or acute pain. Chronic pain can arise from many sources including, cancer, Reflex Sympathetic Dystrophy Syndrome (RSDS), and migraine. Acute pain is typically directly related to tissue damage, and lasts for a relatively short amount of time, e.g., hours to days, or up to 7 days. In other embodiments, the pain is breakthrough cancer pain.

In some aspects, the present invention provides methods of managing or treating chronic pain in a subject. In some embodiments, the subject is opioid experienced, opioid tolerant or opioid naive, as defined above. In a specific embodiment, the subject is opioid tolerant. In another embodiment, the subject has not responded to previous treatment with the maximal doses of non-steroidal anti-inflammatory drugs.

In some embodiments, the chronic pain is chronic lower back pain (CLBP). In some embodiments, the chronic lower back pain is moderate to severe chronic lower back pain. In other embodiments, the pain is neuropathic pain or osteoarthritic pain. In a specific embodiment, the subject to be treated for moderate to severe chronic low back pain is an opioid experienced subject.

It has also been presently found that twice daily (or once daily) administration of low doses of buprenorphine via transmucosal drug delivery devices of the present invention is associated with low incidence or absence of common opioid adverse effects associated with opioid analgesics. In one embodiment, the adverse effect is nausea. In another embodiment, the adverse effect is constipation.

Administration and Dosing of Buprenorphine

In some embodiments, transmucosal drug delivery devices of the present invention (e.g., BEMA Buprenorphine) are administered once daily or twice daily. In some embodiments, the total daily dose of buprenorphine administered is between 200 μg and 1800 μg, e.g., 200 μg, 220 μg, 240 μg, 280 μg, 300 μg, 320 μg, 350 μg, 360 μg, 400 μg, 450 μg, 480 μg, 500 μg, 550 μg, 600 μg, 620 μg, 650 μg, 700 μg, 720 μg, 750 μg, 800 μg, 860 μg, 900 μg, 960 μg, 1000 μg, 1100 μg, 1200 μg, 1250 μg, 1300 μg, 1400 μg, 1500 μg, 1600 μg, and 1800 μg.

In some embodiments, the transmucosal drug delivery devices of the present invention comprise low doses of buprenorphine. In one embodiment, the low dose of buprenorphine contained in the devices is defined as the dose of about 100 μg to about 900 μg of buprenorphine. In some embodiments, the low dose of buprenorphine comprised in the mucoadhesive device of the invention is 100 μg, 110 μg, 120 μg, 140 μg, 150 μg, 160 μg, 175 μg, 180 μg, 200 μg, 225 μg, 240 μg, 250 μg, 275 μg, 300 μg, 310 μg, 325 μg, 350 μg, 360 μg, 375 μg, 400 μg, 430 μg, 450 μg, 480 μg, 500 μg, 550 μg, 600 μg, 625 μg, 650 μg, 700 μg, 750 μg, 800 μg, 900 μg, 1000 μg, 1200 μg, 1250 μg, 1300 μg, 1400 μg, 1500 μg, 1600 μg, and 1800 μg.

Transmucosal Pharmaceutical Delivery Device

Preparation of transmucosal pharmaceutical delivery devices have been previously described, e.g., in U.S. patent application Ser. No. 08/734,519, filed on Oct. 18, 1996, now U.S. Pat. No. 5,800,832, issued Sep. 1, 1998; U.S. patent application Ser. No. 09/144,827, filed on Sep. 1, 1998, now U.S. Pat. No. 6,159,498, issued on Dec. 12, 2000; U.S. patent application Ser. No. 11/069,089, filed on Mar. 1, 2005, Now U.S. Pat. No. 7,579,019, issued on Aug. 25, 2009; U.S. patent application Ser. No. 11/639,408, filed on Dec. 13, 2006, published as US 2007/0148097; U.S. patent application Ser. No. 11/817,915, filed on Sep. 6, 2007, published as US 2010/0015183; U.S. patent application Ser. No. 13/834,306, filed on Jul. 15, 2011, now U.S. Pat. No. 8,147,866, issued on Apr. 3, 2012; U.S. patent application Ser. No. 13/590,094, filed on Aug. 20, 2012; U.S. patent application Ser. No. 12/537,571, filed on Aug. 7, 2009, published as US 2011/0033541; and U.S. patent application Ser. No. 12/537,580, filed on Aug. 7, 2009, published as US 2011/0033542, the entire contents of which are incorporated herein by reference.

i. Mucoadhesive Layer

In some embodiments, the devices of the present invention adhere to a mucosal surface of the subject within about 5 seconds following application. In some embodiments, the devices of the present invention comprise an opioid agonist. In some embodiments, the devices of the present invention include a bioerodable- or water-erodable mucoadhesive layer, and the opioid agonist is comprised in the mucoadhesive layer. In one embodiment, the opioid agonist is buprenorphine. The dose of buprenorphine that can be incorporated into the device of the present invention depends on the desired treatment dosage to be administered and can range from about 20 μg to about 20 mg, or from about 120 μg to about 2000 μg of buprenorphine.

ii. Backing Layer

In some embodiments, the device further comprises at least one additional non-adhesive polymeric environment, e.g., a backing layer. This layer is disposed adjacent to the mucoadhesive polymeric diffusion environment, e.g., a backing layer, functions to facilitate the delivery of the opioid agonist, such as buprenorphine, to the mucosa. This additional layer may comprise the same or a different combination of polymers as the mucoadhesive polymeric diffusion environment or the non-adhesive polymeric diffusion environment.

In some embodiments, the backing layer includes an additional medicament, such as an opioid antagonist, to render the device of the invention abuse-resistant. In some embodiments, the opioid antagonist is naloxone. The dose of naloxone that can be incorporated into the backing layer of the device of the present invention can range from about 2.5 μg to about 5 mg of naloxone. In some embodiments, the amount of buprenorphine and the amount of naloxone disposed in the device are present in a ratio chosen such that the effect of buprenorphine is negated by naloxone if the mixture is injected or snorted. In some embodiments, the amount of buprenorphine and the amount of naloxone disposed in the device are present in a 4:1 w/w ratio.

EXEMPLIFICATION OF THE INVENTION

The invention will be further understood by the following examples. However, those skilled in the art will readily appreciate that the specific experimental details are only illustrative and are not meant to limit the invention as described herein, which is defined by the claims which follow thereafter.

Example 1

Preparation of the Devices of the Invention

Transmucosal devices are configured in the form of a disc, rectangular in shape with round corners, yellow on one or both sides of the cheek). Buprenorphine is present in the mucoadhesive layer, and this side is to be placed in contact with the buccal mucosa (inside the cheek). The drug is delivered into and across the mucosa as the disc erodes in the mouth. The non-adhesive, backing layer controls the rate erosion of the disc, and minimizes the amount of buprenorphine dissolved in saliva and ultimately swallowed, a pathway of lower absorption due first pass metabolism. The mucoadhesive polymeric diffusion layer and the backing layer are bonded together and do not delaminate during or after application.

The mucoadhesive layer for the transmucosal devices of the present invention comprising the desired dosage of buprenorphine is prepared by mixing purified water, propylene glycol (about 4.6% total formulation, by dry weight), sodium benzoate (about 0.5% total formulation, by dry weight), methylparaben (about 0.9% total formulation, by dry weight), propylparaben (about 0.2% total formulation, by dry weight), vitamin E acetate (about 0.06% total formulation, by dry weight), citric acid (about 0.5% total formulation, by dry weight), yellow iron oxide (about 0.5% total formulation, by dry weight), monobasic sodium phosphate (about 3.4% total formulation, by dry weight). The above ingredients are added sequentially to a mixing vessel. After the components are dissolved, buprenorphine HCl (about 1.3% total formulation, by dry weight) is added, and the vessel was heated to 120° F. to 130° F. After dissolution, the polymer mixture (hydroxypropyl cellulose (about 6.8% total formulation, by dry weight), hydroxyethyl cellulose (about 20.3% total formulation, by dry weight), polycarbophil (about 6.3% total formulation, by dry weight), and carboxy methyl cellulose (about 54.3% total formulation, by dry weight)) are added to the vessel, and stirred until dispersed. Subsequently, heat is removed from the mixing vessel. As the last addition step, tribasic sodium phosphate and sodium hydroxide are added to adjust the blend to a desired pH. The blend is mixed under vacuum for a few hours. Each prepared mixture is stored in an air-sealed vessel until its use in the coating operation.

The backing layer is prepared by adding purified water to a mixing vessel followed by sequential addition of sodium benzoate (about 0.5% total formulation, by dry weight), methylparaben (about 0.4% total formulation, by dry weight), propylparaben (about 0.1% total formulation, by dry weight), citric acid (about 0.5% total formulation, by dry weight), vitamin E acetate (about 0.05% total formulation, by dry weight), sodium saccharin (about 0.5% total formulation, by dry weight). Subsequently, a mixture of the polymers hydroxypropyl cellulose (about 63% total formulation, by dry weight) and hydroxyethyl cellulose (about 32% total formulation, by dry weight) are added and stirred at a temperature between about 120° F. and 130° F., until evenly dispersed. Upon cooling to room temperature, titanium dioxide (about 2.5% total formulation, by dry weight) and peppermint oil (about 0.8% total formulation, by dry weight) are then added to the vessel and stirred. The prepared mixture is stored in an air-sealed vessel until it is ready for use in the coating operation.

The layers are cast in series onto a St. Gobain polyester liner. First, the backing layer is cast using a knife-on-a-blade coating method. The backing layer is then cured in a continuous oven at about 65° C. to 95° C. and dried. After two coating and drying iterations, an approximately 8 mil (203 to 213 micrometers) thick backing layer is obtained. Subsequently, the mucoadhesive polymeric diffusion environment is cast onto the backing layer, cured in an oven at about 65° C. to 95° C. and dried. The devices are then die-cut by kiss-cut method and removed from the casting surface.

Example 2

Placebo-Controlled, Double-Blind Study to Evaluate the Efficacy of BEMA Buprenorphine in Subjects with Moderate to Severe Chronic Low Back Pain A 12-week, placebo-controlled, double-blind randomized withdrawal study was conducted to evaluate the efficacy and safety of buprenorphine delivered twice daily via transmucosal drug delivery device with enhanced uptake (BEMA buprenorphine) in subjects with moderate to severe chronic low back pain. The study was also designed to define the range of BEMA Buprenorphine doses effective for management of moderate to severe chronic lower back pain.

i. Study Design

The study consisted of an open-label dose titration period lasting up to 4 weeks, followed by a randomized, double-blind, placebo-controlled treatment period of 12 weeks. The subjects continued on their current pain therapy during the initial screening period (days −14 to −1) and until 12 to 24 hours prior to Day 0/1 of the open-label dose titration period. Predose assessments were performed on open-label titration period Day 0 and the first dose of study drug was taken on open-label titration period Day 1.

During the open-label titration period, the subjects were administered BEMA Buprenorphine approximately every 12 hours, and dose adjustments were performed at intervals over a period of up to 4 weeks until a stabilized dose was found (i.e., the dose that provided meaningful pain relief and was well tolerated). The titration sequence of BEMA Buprenorphine is illustrated in the Table 4 below. The subjects for whom a stabilized dose could not be found were discontinued from the study.

TABLE 4

| BEMA Buprenorphne Titration Schedule | |
|---|---|
| Study Days | Titration Sequence - BEMA Buprenorphine Low Dose (Q12 hours) |
| 1 | A |
| 7 (±3 days) | 2xA |
| 14 (±3 days) | 3xA |
| 21 (±3 days) | 4xA |

Figure 1:
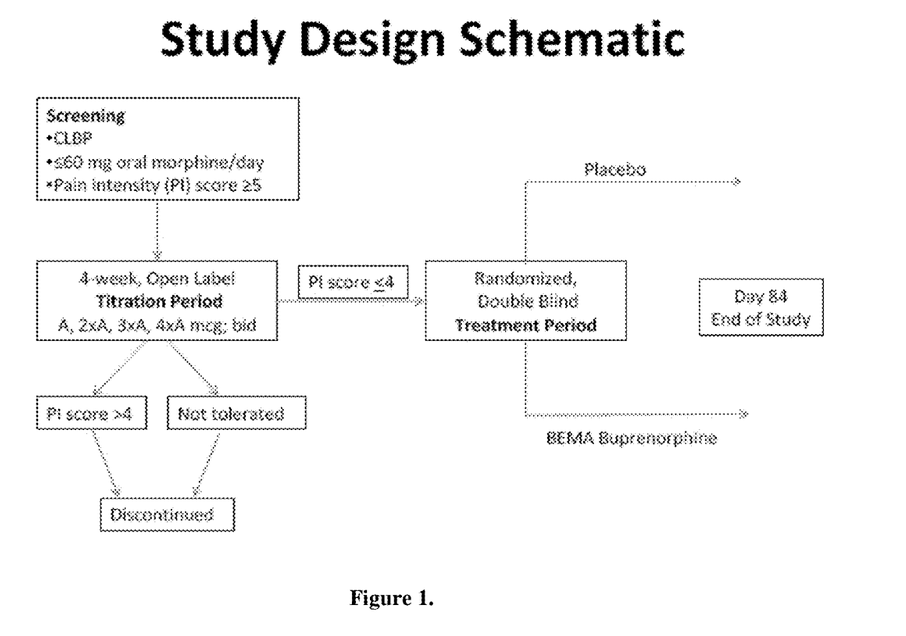
FIG. 1 is a schematic representation of the design of a clinical study for evaluating the efficacy and safety of twice daily administration of BEMA buprenorphine in subjects with chronic low back pain.

The subjects for whom a stabilized dose was identified and who had taken that dose at least 12 times over the last 7 days entered a 12-week, double-blind treatment period, in which half of subjects received BEMA Placebo and half continued receiving BEMA Buprenorphine at the stabilized dose. Each subject's participation in the entire study lasted 19 weeks. The schematic showing the study design is shown in FIG. 1.

ii. Subject Population Used in the Study

The subjects who were selected for the inclusion in the study were opioid naive or opioid experienced, as defined earlier in this application. Opioid experienced subjects were subjects taking ≤60 mg oral daily dose of morphine or equianalgesic dose of another allowed opioid for 1 week or longer. Opioid naive subjects were not taking any opioids for 1 week or longer.

Figure 2:
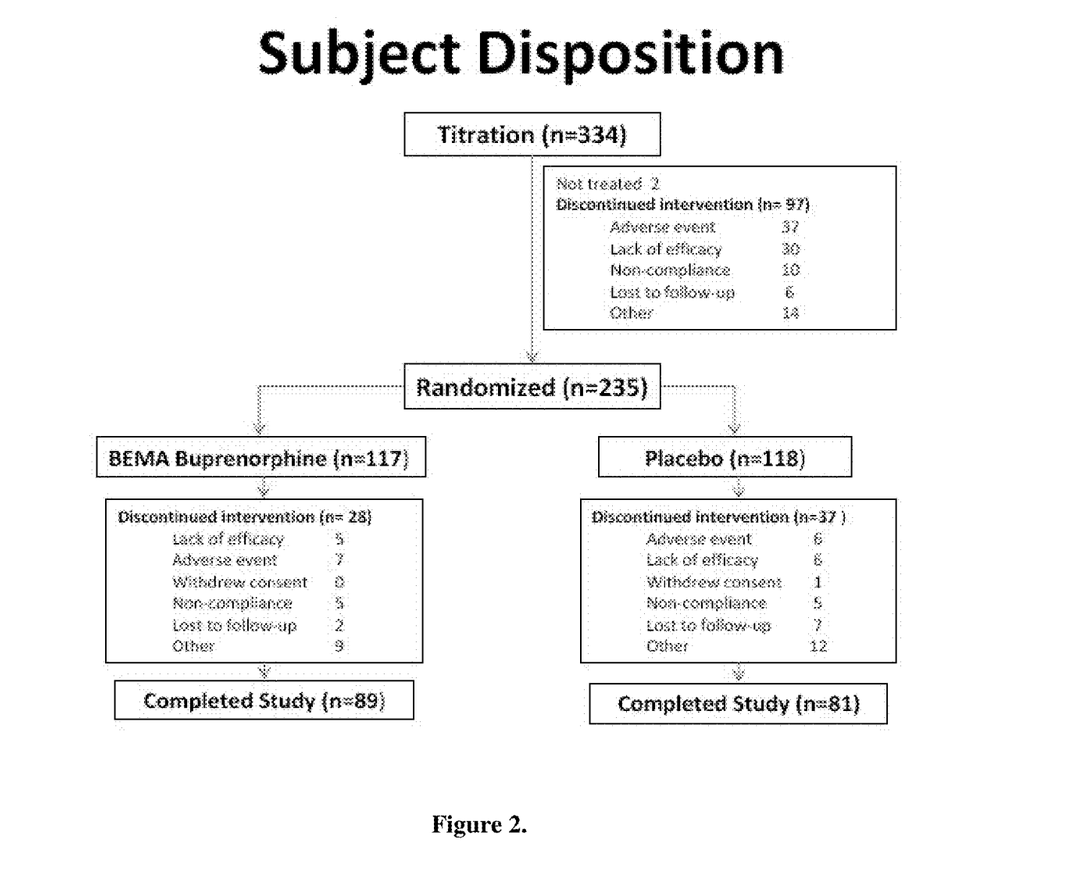
FIG. 2 is a schematic representation of disposition of subjects who participated in the clinical study to evaluate the efficacy and safety of twice daily administration of BEMA buprenorphine in subjects with chronic low back pain.

A total of 334 subjects entered the study, of which 332 subjects entered the 4-week open-label dose titration period. As 97 subjects discontinued intervention during the open-label titration period, a total of 235 subjects continued on to the 12-week double-blind treatment period. Of the 117 subjects who received BEMA Buprenorphine, 28 discontinued intervention, and 89 subjects completed the study. Of the 118 subjects who received placebo, 37 discontinued intervention, and 81 subjects completed the study. Subject disposition during the study is summarized in FIG. 2, and the characteristics of the population who participated in the study are summarized in the Table 5 below:

TABLE 5

| Study Population Characteristics | | | |
|---|---|---|---|
| | Open Label Titration BEMA Buprenorphine | Double Blind Treatment BEMA Buprenorphine | Double Blind Treatment Placebo |
| Number of subjects | 332 | 117 | 118 |
| Mean Age (yrs.) | 51 | 51 | 51 |
| Women, n (%) | 55.5 | 53 | 56 |
| Opioid Naive (%) | 62.7 | 62.4 | 69.5 |
| Mean Pain Intensity at Screening | 7 | | |
| Mean Pain Intensity at Baseline | NA | 3.23 | 3.26 | iii. Analgesic Efficacy of BEMA Buprenorphine

Analgesic efficacy was assessed daily by having the subject record their average pain intensity over the past 24 hours on a scale of 0 to 10, where 0 represents no pain and 10 represents the worst pain imaginable (11-point Numerical Rating Scale, NRS). The mean change in daily pain intensity from baseline (CBL) to final visit during double blind treatment period is presented in Tables 6-12 below. Tables 6-8 present the mean change data for different subject groups, and Tables 9-12 present the mean change data for the subject groups treated with different doses of buprenorphine.

TABLE 6

| Average Daily Pain Intensity - All Subjects | | |
|---|---|---|
| Parameter | BEMA Buprenorphine | Placebo |
| Number of subjects | 117 | 118 |
| Primary Analysis, mean (SD) | | |
| Baseline | 3.23 (1.19) | 3.26 (1.22) |
| Final | 3.59 (1.91) | 3.77 (2.22) |
| Least Squares Mean Difference | 0.35 | 0.51 |
| Treatment comparison of Change from Baseline (CBL) Beta Buprenorphine (CBL BB) minus placebo | −0.16 | |
| p-value | 0.53 | |

TABLE 7

| Average daily pain intensity -opioid experienced subjects | | |
|---|---|---|
| Parameter | BEMA Buprenorphine | Placebo |
| Number of subjects | 44 | 36 |
| Primary Analysis, mean (SD) | | |
| Baseline | 3.50 (1.14) | 3.43 (0.87) |
| Final | 4.05 (2.04) | 4.86 (2.03) |
| Least Squares Mean Difference | 0.57 | 1.41 |
| Treatment comparison of CBL BB minus placebo | −0.84 | |
| p-value | 0.067 | |

TABLE 8

| Average daily pain intensity in opioid naive subjects | | |
|---|---|---|
| Parameter | BEMA Buprenorphine | Placebo |
| Number of subjects | 73 | 82 |
| Primary Analysis, mean (SD) | | |
| Baseline | 3.07 (1.20) | 3.19 (1.33) |
| Final | 3.31 (1.78) | 3.29 (2.1) |
| Least Squares Mean Difference | 0.21 | 0.13 |
| Treatment comparison of CBL BB minus placebo | 0.08 | |
| p-value | 0.78 | |

As shown in Table 7, the change from baseline in average daily pain score on BEMA Buprenorphine compared to placebo is nearly statistically significant in the opioid experienced population.

TABLE 9

Average daily pain intensity in subjects treated
with the daily dose of A μg of buprenorphine

| Parameter | BEMA Buprenorphine Dose A mcg | Placebo |
|---|---|---|
| N | 28 | 33 |
| Primary Analysis, mean (SD) | | |
| Baseline | 2.79 (1.51) | 3.12 (1.38) |
| Final | 3.58 (1.79) | 2.88 (2.18) |
| Least Squares Mean Difference | 0.72 | −0.24 |
| Treatment comparison of CBL BB minus placebo | 0.90 | |
| p-value | 0.085 | |

TABLE 10

Average daily pain intensity in subjects treated
with the daily dose of 2xA μg of buprenorphine

| Parameter | BEMA Buprenorphine Dose 2xA mcg | Placebo |
|---|---|---|
| N | 31 | 33 |
| Primary Analysis, mean (SD) | | |
| Baseline | 3.25 (1.13) | 3.33 (1.12) |
| Final | 3.23 (1.73) | 4.04 (2.27) |
| Least Squares Mean Difference | −0.03 | 0.72 |
| Treatment comparison of CBL BB minus placebo | −0.74 | |
| p-value | 0.17 | |

TABLE 11

Average daily pain intensity in subjects treated
with the daily dose of 3xA μg of buprenorphine

| Parameter | BEMA Buprenorphine Dose 3xA mcg | Placebo |
|---|---|---|
| N | 22 | 31 |
| Primary Analysis, mean (SD) | | |
| Baseline | 3.43 (0.87) | 3.48 (1.25) |
| Final | 4.24 (2.48) | 4.0 (2.23) |
| Least Squares Mean Difference | 0.79 | 0.53 |
| Treatment comparison of CBL BB minus placebo | 0.26 | |
| p-value | 0.70 | |

TABLE 12

Average daily pain intensity in subjects treated
with the daily dose of 4xA μg of buprenorphine

| Parameter | BEMA Buprenorphine Dose 4xA mcg | Placebo |
|---|---|---|
| N | 36 | 21 |
| Primary Analysis, mean (SD) | | |
| Baseline | 3.45 (1.09) | 3.04 (1.05) |
| Final | 3.69 (1.75) | 4.27 (1.92) |
| Least Squares Mean Difference | 0.29 | 1.13 |
| Treatment comparison of CBL BB minus placebo | −0.84 | |
| p-value | 0.11 | |

Figure 3:
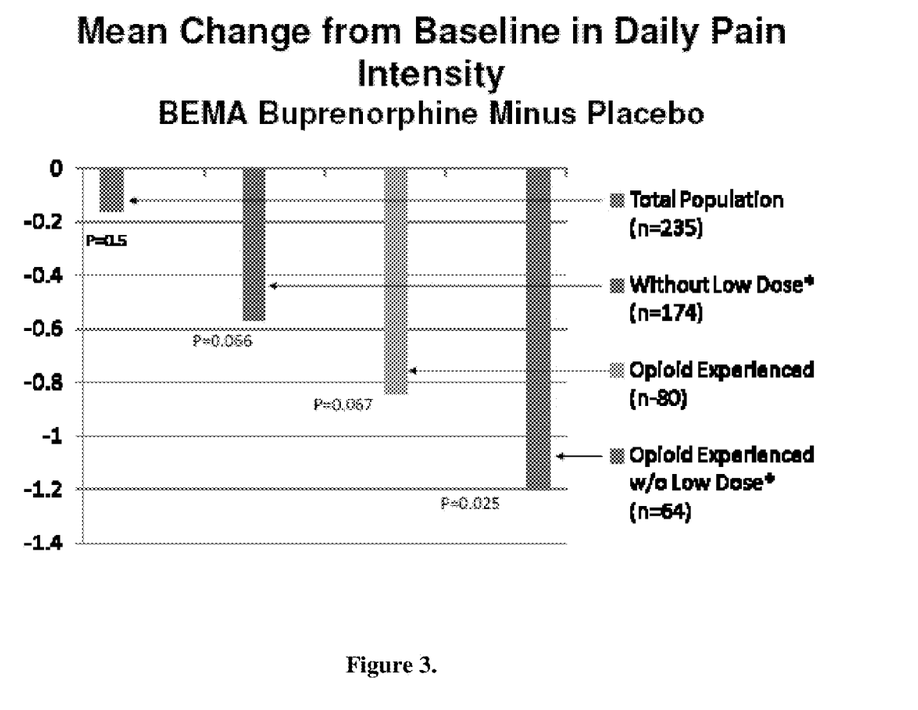
FIG. 3 is a graph showing mean change from baseline in daily pain intensity experienced by the subjects with chronic low back pain after twice daily administration of BEMA buprenorphine.

Graphed in FIG. 3 is the mean change from baseline in daily pain intensity for all subjects; all subjects receiving 2xA μg, 3xA μg, or 4xA μg, BEMA Buprenorphine; all opioid experienced subjects; and all opioid experienced subjects receiving 2xA μg, 3xA μg, or 4xA μg BEMA Buprenorphine.

iv. Incidence of Adverse Events

Adverse events (AE) were recorded for all subjects in the study. AE was defined as any untoward medical occurrence in a patient or clinical investigation subject administered a pharmaceutical product and which does not necessarily have a causal relationship with this treatment. The total number of adverse events recorded for both the open label titration and double blind treatment periods are listed in the Table 13 below.

TABLE 13

Total Treatment Emergent Adverse Events (TEAEs)

| Adverse event profile | Open Label Titration BEMA Buprenorphine, n (%) | Double Blind Treatment BEMA Buprenorphine n (%) | Placebo n (%) |
|---|---|---|---|
| Subjects with ≥1 AE | 219 (66) | 73 (62) | 68 (58) |
| Subjects with ≥1 AE causing discontinuation | | 6 (5) | 3 (2) |
| Discontinued due to opioid withdrawal | | | |
| Subjects with ≥1 SAE | | 1 (1) | 0 |
| AEs reported in >5% of subjects | | | |
| Nausea | 108 (32) | 11 (9) | 10 (8) |
| Vomiting | 20 (6) | 6 (5) | 4 (3) |
| Constipation | 36 (11) | 7 (6) | 3 (2) |
| Dizziness | 30 (9) | 4 (3) | 1 (1) |
| Headache | 39 (12) | 12 (10) | 5 (4) |

The intensity of AEs was characterized as mild, moderate, or severe as follows:

Mild: AEs that were transient, did not require a special treatment and did not interfere with the subject's daily activities.

Moderate: AEs that introduced a low level of inconvenience or concern to the subject and could interfere with daily activities, but were usually ameliorated by simple therapeutic measures.

Severe: AEs that interrupted a subject's usual daily activity and typically required systemic drug therapy or other treatment.

Table 14 below shows the number and percent of subjects who experienced TEAEs during the open label titration period involving 330 subjects, with all TEAEs characterized by event intensity and relationship to the study drug. Table 15 below shows analogous data for the double blind treatment period and buprenorphine treatment group involving 117 subjects. The maximum intensity ever recorded for each event and the drug relationship at that intensity were used to categorize adverse events. "Drug-related" category is listed as "R" and includes adverse events with investigator-assessed relation to drug of "probably" or "possibly". "Non drug-related" category is listed as "NR".

TABLE 14

TEAEs by Event Intensity and Drug Relationship During Open Label Titration Period.

| AE Profile | Mild | | Moderate | | Severe | | Not Reported | | Overall | |
|---|---|---|---|---|---|---|---|---|---|---|
| | R n (%) | NR n (%) | R n (%) | NR n (%) | R n (%) | NR n (%) | R n (%) | NR n (%) | R n (%) | NR n (%) |
| No. of subject with ≥1 TEAE | 49 (14.8) | 52 (15.8) | 63 (19.1) | 34 (10.3) | 12 (3.6) | 10 (3.0) | 0 | 0 | 124 (37.6) | 96 (29.1) |
| Constipation | 23 (7.0) | 4 (1.2) | 5 (1.5) | 1 (0.3) | 3 (0.9) | 0 | 0 | 0 | 31 (9.4) | 5 (1.5) |
| Nausea | 50 (15.2) | 9 (2.7) | 42 (12.7) | 1 (0.3) | 5 (1.5) | 1 (0.3) | 0 | 0 | 97 (29.4) | 11 (3.3) |
| Vomiting | 3 (0.9) | 6 (1.8) | 7 (2.1) | 0 | 2 (0.6) | 1 (0.3) | 0 | 0 | 12 (3.6) | 7 (2.1) |
| Dizziness | 13 (3.9) | 3 (0.9) | 10 (3.0) | 1 (0.3) | 3 (0.9) | 0 | 0 | 0 | 26 (7.9) | 4 (1.2) |
| Headache | 15 (4.5) | 9 (2.7) | 8 (2.4) | 3 (0.9) | 3 (0.9) | 1 (0.3) | 0 | 0 | 26 (7.9) | 13 (3.9) |

TABLE 15

TEAEs by Event Intensity and Drug Relationship During Double Blind Treatment Period.

| AE Profile | Mild | | Moderate | | Severe | | Not Reported | | Overall | |
|---|---|---|---|---|---|---|---|---|---|---|
| | R n (%) | NR n (%) | R n (%) | NR n (%) | R n (%) | NR n (%) | R n (%) | NR n (%) | R n (%) | NR n (%) |
| No. of subject with ≥1 TEAE | 9 (7.7) | 24 (20.5) | 11 (9.94) | 23 (19.7) | 1 (0.9) | 5 (4.3) | 0 | 0 | 21 (17.9) | 52 (44.4) |
| Constipation | 3 (2.6) | 0 | 4 (3.4) | 0 | 0 | 0 | 0 | 0 | 7 (6.0) | 0 |
| Nausea | 5 (4.3) | 3 (2.6) | 3 (2.6) | 0 | 0 | 0 | 0 | 0 | 8 (6.8) | 3 (2.6) |
| Vomiting | 0 | 2 (1.7) | 2 (1.7) | 1 (0.9) | 1 (0.9) | 0 | 0 | 0 | 3 (2.6) | 3 (2.6) |
| Dizziness | 1 (0.9) | 0 | 2 (1.7) | 0 | 1 (0.9) | 0 | 0 | 0 | 4 (3.4) | 0 |
| Headache | 1 (0.9) | 7 (0.6) | 2 (1.7) | 1 (0.9) | 0 | 1 (0.9) | 0 | 0 | 3 (2.6) | 9 (7.7) |

Example 3

Pharmacokinetic Profiles for BEMA Buprenorphine

Pharmacokinetic parameters for the BEMA Buprenorphine doses used in the treatment of chronic pain were determined in a separate, multiple dose study. BEMA Buprenorphine contained buprenorphine doses of 2×A µg, and 4×A µg. Each dose was administered twice daily for 3 days with serial blood samples collected. Selected pharmacokinetic parameters are shown in the Table 16 below.

TABLE 16

Selected Pharmacokinetic Parameters for BEMA Buprenorphine Buccal Films comprising 1xA µg, 2xA µg, 3xA µg and 4xA µg buprenorphine

| Pharmacokinetic Parameters (Mean values) | 1xA µg | 2xA µg | 3xA µg | 4xA µg |
|---|---|---|---|---|
| $T_{max}$ (hr) | 2.90 | 2.61 | 2.00 | 2.20 |
| $C_{max}$ (ng/mL) | 0.0766 | 0.156 | 0.216 | 0.364 |
| $C_{min}$ (ng/mL) | 0.0157 | 0.0371 | 0.0558 | 0.0862 |
| $C_{avg}$ (ng/mL) | 0.0409 | 0.0805 | 0.113 | 0.195 |
| $AUC_{0-\tau}$ (hr*ng/mL) | 0.4903 | 0.9658 | 1.358 | 2.343 |
| $AUC_{last}$ (hr*ng/mL) | 0.4085 | 0.7902 | 1.111 | 5.033 |

$T_{max}$ refers to the time to reach the steady-state $C_{max}$ of plasma buprenorphine concentration.
$C_{max}$ refers to the maximum concentration in plasma in steady-state.
$C_{min}$ refers to the minimum concentration in plasma in steady-state.
$C_{avg}$ refers to the average concentration in plasma in steady-state.
$AUC_{0-\tau}$ refers to the area under the plasma concentration time curve from time-zero through the dosing interval
$AUC_{last}$ refers to the area under the concentration-time curve from time-zero to the time of the last quantifiable concentration.

What is claimed is:

1. A method of treating chronic pain, the method comprising:
   administering to a subject in need thereof a mucoadhesive bioerodable drug delivery device, wherein the device is administered once or twice daily,
   wherein the device comprises:
      a bioerodable mucoadhesive layer comprising about 100 g to about 0.9 mg buprenorphine and buffered to a pH of between about 4.0 and about 6.0; and
      a backing layer buffered to a pH of between about 4.0 and about 4.8 and that does not include an opioid antagonist;
   wherein the device provides a steady-state $C_{max}$ of plasma buprenorphine concentration in a range between about 0.156 and about 0.364 ng/mL;
   wherein the subject is an opioid-experienced subject; and
   wherein the subject treated experiences mild or moderate common opioid adverse effects, or no common opioid adverse effects.

2. The method according to claim 1, wherein the device is administered once daily.

3. The method according to claim 1, wherein the chronic pain is chronic low back pain.

4. The method according to claim 1, wherein the chronic pain is moderate to severe chronic low back pain.

5. The method according to claim 1, wherein the subject is treated without significant constipation.

6. The method according to claim 1, wherein the subject is treated without significant nausea.

7. The method according to claim 1, wherein the total daily dose of buprenorphine administered to the subject is selected from the group consisting of 200 g, 220 g, 240 g, 280 g, 300 g, 320 g, 350 g, 360g, 400 g, 450 g, 480 g, 500 g, 550 g, 600 g, 620 g, 650 g, 700 g, 720 g, 750 g, 800 g, 860 g, 900 g, 960 g, 1000 g, 1100 g, 1200 g, 1250 g, 1300 g, 1400 g, 1500 g, 1600 g, and 1800 g of buprenorphine.

8. The method according to claim 1, wherein the mucoadhesive bioerodable drug delivery device further comprises a barrier layer comprising:
a polymeric barrier environment disposed adjacent to the mucoadhesive layer to provide a unidirectional gradient upon application to a mucosal surface for the rapid and efficient delivery of buprenorphine,
wherein the unidirectional gradient delivers buprenorphine across the buffered polymeric diffusion environment upon application to the mucosal surface.

9. A method of treating a subject with moderate to severe chronic low back pain, comprising:
administering to the subject twice daily a mucoadhesive bioerodable drug delivery device to an oral mucosal surface of the subject, the device comprising:
a bioerodable mucoadhesive layer comprising an effective amount of buprenorphine disposed in a buffered polymeric diffusion environment, wherein the polymeric diffusion environment is a buffered environment having a pH of between about 4 and about 6; and
a backing layer buffered to a pH between about 4.0 and about 4.8 and that does not include an opioid antagonist;
wherein the total daily dose of buprenorphine administered to the subject is effective for treating moderate to severe chronic low back pain;
wherein the subject is an opioid-experienced subject; and
wherein the subject treated experiences mild or moderate common opioid adverse effects, or no common opioid adverse effects.

10. The method according to claim 1, wherein said chronic pain is neuropathic pain.

11. The method according to claim 1, wherein said chronic pain is osteoarthritic pain.

12. The method according to claim 1, wherein the device comprises a dose of buprenorphine selected from the group consisting of 100 g, 110 g, 120 g, 140 g, 150 g, 160 g, 175 g, and 180g.

13. The method according to claim 1, wherein the total daily dose of buprenorphine administered to the subject ranges from 200 g to about 1800 µg.

14. The method according to claim 1, wherein steady-state $T_{max}$ of buprenorphine is in a range between about 2.00 and about 2.90 h.

15. The method according to claim 1, wherein $C_{min}$ of buprenorphine is in a range between about 0.0157 and about 0.0862 ng/mL.

16. The method according to claim 1, wherein steady-state $AUC_{last}$ of buprenorphine is in a range between about 0.4085 and about 5.033 h*ng/mL.

17. The method according to claim 1, wherein between about 2.4-6.9% of subjects experience drug related mild or moderate headaches as a treatment emergent adverse event (TEAE).

18. The method according to claim 1, wherein between about 3-6.9% of subjects experience drug related mild or moderate dizziness as a TEAE.

19. The method according to claim 1, wherein between about 2.6-27.9% of subjects experience drug related mild or moderate nausea as a TEAE.

20. The method according to claim 1, wherein between about 1.5-8.5% of subjects experience drug related mild or moderate constipation as a TEAE.

21. The method according to claim 1, wherein between about 0.9-3% of subjects experience drug related mild or moderate vomiting as a TEAE.

22. The method according to claim 1, wherein between about 7.7-33.9% of subjects experience drug related mild or moderate TEAEs.

* * * * *

UNITED STATES PATENT AND TRADEMARK OFFICE
CERTIFICATE OF CORRECTION

PATENT NO. : 9,901,539 B2
APPLICATION NO. : 13/724959
DATED : February 27, 2018
INVENTOR(S) : Andrew Finn et al.

It is certified that error appears in the above-identified patent and that said Letters Patent is hereby corrected as shown below:

In the Claims

In Claim number 1, at Column 16, Line number 43, delete "100 g" and insert --100 μg--

In Claim number 7, at Column 16, Line 66 to Column 17, Line 3, delete "200 g, 220 g, 240 g, 280 g, 300 g, 320 g, 350 g, 360g, 400 g, 450 g, 480 g, 500 g, 550 g, 600 g, 620 g, 650 g, 700 g, 720 g, 750 g, 800 g, 860 g, 900 g, 960 g, 1000 g, 1100 g, 1200 g, 1250 g, 1300 g, 1400 g, 1500 g, 1600 g, and 1800 g" and insert --200 μg, 220 μg, 240 μg, 280 μg, 300 μg, 320 μg, 350 μg, 360 μg, 400 μg, 450 μg, 480 μg, 500 μg, 550 μg, 600 μg, 620 μg, 650 μg, 700 μg, 720 μg, 750 μg, 800 μg, 860 μg, 900 μg, 960 μg, 1000 μg, 1100 μg, 1200 μg, 1250 μg, 1300 μg, 1400 μg, 1500 μg, 1600 μg, and 1800 μg--

In Claim number 12, at Column 18, Line numbers 5-6, delete "100 g, 110 g, 120 g, 140 g, 150 g, 160 g, 175 g, and 180g." and insert --100 μg, 110 μg, 120 μg, 140 μg, 150 μg, 160 μg, 175 μg, and 180 μg.--

In Claim number 13, at Column 18, Line number 9, delete "200 g" and insert --200 μg--

Signed and Sealed this
Twenty-ninth Day of May, 2018

Andrei Iancu
*Director of the United States Patent and Trademark Office*